United States Patent [19]

Miettinen et al.

[11] Patent Number: 5,502,045
[45] Date of Patent: Mar. 26, 1996

[54] USE OF A STANOL FATTY ACID ESTER FOR REDUCING SERUM CHOLESTEROL LEVEL

[75] Inventors: Tatu Miettinen; Hannu Vanhanen, both of Helsinki; Ingmar Wester, Raisio, all of Finland

[73] Assignee: Raision Tehtaat Oy AB, Raisio, Finland

[21] Appl. No.: 140,085

[22] PCT Filed: May 3, 1991

[86] PCT No.: PCT/FI91/00139

§ 371 Date: Nov. 22, 1993

§ 102(e) Date: Nov. 22, 1993

[87] PCT Pub. No.: WO92/19640

PCT Pub. Date: Nov. 12, 1992

[51] Int. Cl.⁶ ............................................. A61K 31/56
[52] U.S. Cl. ............................................. 514/182
[58] Field of Search ................................. 514/182

[56] References Cited

U.S. PATENT DOCUMENTS

| 3,004,043 | 10/1961 | Stern | 260/397.2 |
| 5,244,887 | 9/1993 | Straub | 514/182 |
| 5,270,041 | 12/1993 | Eugster et al. | 424/195.1 |

FOREIGN PATENT DOCUMENTS

| 0195311 | 9/1986 | European Pat. Off. . |
| 0289636 | 11/1988 | European Pat. Off. . |
| 2035069 | 1/1971 | Germany . |
| 2422317 | 11/1974 | Germany . |

OTHER PUBLICATIONS

Chemical Abstracts, vol. 115, No. 1, 8 Jul. 1991, T. Heinemann et al., "Mechanisms of Action of Plant Sterols on Inhibition of Cholesterol Absorption: Comparison of Sitosterol and Sitostanol".

Chemical Abstracts, vol. 112, No. 7, 12 Feb. 1990, I. Ikeda et al., "Effects of Sitosterol and Sitostanol on Micellar Solubility of Cholesterol".

Chemical Abstracts, vol. 112, No. 7, 2 Feb. 1990, T. Heinemann et al., "Comparison of Sitosterol and Sitostanol on Inhibition of Intestinal Cholesterol Absorption".

Chemical Abstracts, vol. 95, No. 13, 28 Sep. 1981, I. Ikeda et al., "Antihypercholesterolemic Activity of beta–sitostanol in Rabbits".

Chemical Abstracts, vol. 88, No. 3, 16 Jan. 1978, M. Sugano et al., "A comparison of hypocholesterolemic activity of beta–sitosterol and beta–sitostanol in rats".

Int'l Search Report, dated 11 Dec. 1991 of PCT/FI91/00139.
Int'l Preliminary Exam Report, dated 4 Aug. 1993 of PCT/FI91/00139.
Copy of Written Opinion from Int'l Preliminary Exam Authority, dated 14 Apr. 1993 of PCT/FI91/00139.
Abstract, JP 44 004974, 28 Feb. 1969, "Sitosterol Fatty Acid Ester", Tsuchiya.

*Primary Examiner*—Raymond Henley, III
*Assistant Examiner*—Kevin E. Weddington
*Attorney, Agent, or Firm*—Vickers, Daniels & Young

[57] ABSTRACT

The invention relates to a substance which lowers cholesterol levels in serum and which is a β-sitostanol fatty acid ester or fatty acid ester mixture, and to a method for preparing the same. The substance can be used as such or added to a food.

8 Claims, No Drawings

USE OF A STANOL FATTY ACID ESTER FOR REDUCING SERUM CHOLESTEROL LEVEL

This application is a 371 of PCT/FI91/00139 filed May 03, 1991.

A high cholesterol level in serum can be lowered effectively by altering the intestinal metabolism of lipids. In this case the aim may be to hamper the absorption of triglycerides, cholesterol or bile acids. It has been observed in a number of investigations that certain plant sterols, such as β-sitosterol (24-ethyl-5-cholestene-3β-ol) and its hardened form, β-sitostanol (24-ethyl-5α-cholestane-3β-ol), lower serum cholesterol levels by reducing the absorption of dietary cholesterol from the intestines (1–25). The use of plant sterols can be considered safe, since plant sterols are natural components of vegetable fats and oils. Plant sterols themselves are not absorbed from the intestines, or they are absorbed in very low concentrations. A decreased incidence of coronary disease is clearly associated with a decrease in serum cholesterol, in particular LDL cholesterol. A high serum cholesterol value is the most significant single indicator of the risk of coronary disease.

The degree of cholesterol absorption depends on a hereditary property, apoprotein E-phenotype. Apoprotein E is a protein which belongs to serum lipoproteins and takes part in the transport of cholesterol in the system (26). Of alleles associated with the synthesis of apoprotein E, i.e. the lipoprotein which affects absorption, there are known three types, e2, e3, and e4, which combine in pairs at random. Alleles are capable of forming in total six different combinations. The higher the sum of the subindices, the better absorbable the cholesterol and the higher the level of cholesterol, in particular bad LDL cholesterol, in the serum (27). e4 allele is overrepresented among the hereditary factors of Finns, so that its proportion is almost double as compared with many European populations (28). Finns are indeed exceptionally sensitive to dietary flaws and to fatty and high-cholesterol food (29).

Serum cholesterol levels can be lowered by dietary means, by paying attention to the quantity and type of the fat ingested and to the amount of cholesterol intake. In practice, however, these means do not always lead to a satisfactory end result. Other methods, suitable for the entire population, for reaching serum cholesterol levels lower than the present ones must be searched for. Increasing the fiber content of food is a method of limited effect. The cholesterol-lowering effect of soluble fiber in food is based on the binding and removal of bile acids. Since the absorption of cholesterol is of fundamental significance in the regulation of the cholesterol level in serum, it is logical to aim at developing methods by which the absorption of cholesterol can be prevented or reduced.

Pollak demonstrated that ingested plant sterol lowered the level of serum cholesterol in man (1). The same had previously been observed in experimental animals (2, 3). It has been observed in a number of investigations that large doses of plant sterols lower the levels of serum cholesterol, at best by 10–20% (4, 5). In these experiments, large amounts, up to 24 g/day, of β-sitosterol in crystalline form were used (6). In certain experiments the serum cholesterol level was lowered significantly even with lower doses (7), although a small amount of soluble sitosterol administered in the form of fatty acid esters did not seem to lower serum cholesterol very effectively (8). Sitosterol preparations have in general been well tolerated in long-term use (9).

Natural plant sterols resemble cholesterol in their structure. The differences between a cholesterol molecule and a plant sterol molecule are primarily found in the structure of the side chain of the basic frame. An ordinary diet contains plant sterols 100–300 mg/day. Most of the plant sterol in the diet is β-sitosterol, and approx. one-third is campesterol. Small amounts of saturated 5α-sitostanols are also present in food. Usually the campesterol concentrations in serum in particular reflect the degree of absorption of cholesterol (10, 11, 12). Variation in the amounts of plant sterols in the diet affects the serum cholesterol level, but this is an area which has not been studied much. Plant sterols are poorly absorbed from the intestines. Plant sterols which are scantily absorbed into the system (less than 10% of the sterols) (30, 31, 32) are excreted in the bile and through that in the stools. At present it is easy to measure sterol levels from food, serum or stool samples by gas chromatographic methods. The levels in serum are in part dependent on the plant sterol amounts derived from the diet and in part on the efficiency of the absorption of sterols. In general the plant sterol levels in serum remain below $1/300$ of the serum cholesterol level, since the absorbed plant sterol fraction is excreted from the system in the bile.

Even large ingested doses of plant sterols do not show in serum plant sterol levels. The values remain at the normal level, since in man the plant sterol absorption capacity is rapidly saturated. The serum plant sterol level rises to a detrimental level in a few rare diseases such as cerebrotendinotic xanthomatosis and sitosterolemia (33, 34, 35), in connection with which coronary disease is common. The incidence of these diseases is at maximum a few cases in a population of one million. Not a single case of these diseases has been observed in Finland. High plant sterol values are at times observed in patients suffering from certain hepatic diseases (36).

Studies of the metabolism of cholesterol have shown that sitosterol inhibits the absorption of both endogenic and dietary cholesterol from the intestines (13, 14). As a result of this, the excretion of neutral steroids in the stools increases, which leads to a shortage of cholesterol in the liver and through that to a decreased serum cholesterol level. On the other hand, sitosterol does not affect the absorption of bile acids (13).

On the basis of experiments on animals, it seems that the action of sitosterol is based on its ability to displace dietary cholesterol in bile acid micelli (15, 16, 17). Similar results have also been obtained in man (37). Various plant sterols have been demonstrated to affect in different ways the absorption of cholesterol (19, 38). Previous studies carried out on experimental animals give the impression that sitostanol is the most effective inhibitor of cholesterol absorption (38) and is itself almost nonabsorbable. Furthermore, an uncontrolled study on six subjects showed that free sitostanol (1.5 g/day) lowered the serum cholesterol (mainly LDL cholesterol) in four weeks by as much as 15%. During a pause of two weeks, the cholesterol values returned to the previous levels (20). Most plant sterol preparations contain a number of different plant sterols. The effect of a plant sterol mixture on the absorption of cholesterol varies, as does their own absorption (21, 22, 23).

The studies carried out so far have mainly concentrated on investigating how the form (crystalline, suspension, granular) in which plant sterols are dosed affects their efficacy in lowering serum cholesterol levels. Crystalline plant sterols do not to a significant degree dissolve in the micelli phase in the alimentary canal, and are therefore not capable of efficiently inhibiting cholesterol absorption. Oils and fats are only to a limited degree capable of dissolving free sterols. Only in a dissolved form do sterols inhibit the absorption of cholesterol. According to Heinemann and coworkers (24), sitostanol inhibited in an infusion experiment the absorption of cholesterol 82% whereas sitosterol respectively inhibited the absorption 50%.

In certain studies, fatty acid esters of sitosterol, such as sitosterol acetate or oleate or stigmasterol oleate dissolved in fat, have been used. In experiments on rats an "oil" of this type, having a sterol concentration up to 8%, reduced the absorption of cholesterol by 20–40% (22). During a high-cholesterol diet (500 mg/day), sitosterol oleate (2 g/day) dissolved in fat decreased the absorption of cholesterol in the test subjects on average by 33% (25). In the same study, sitosterol mixed with food and in a lower dose (1 g/day) decreased the absorption of cholesterol by 42%.

A German patent (Deutsches Patentamt, Offenlegungsschrift 2035069/Jan. 28, 1971) relates to the adding of plant sterol fatty acid esters to cooking oil with the objective of lowering the serum cholesterol levels in man. The said patent proposes for use in the esterification of free sterols a method which in no case fulfills the requirements for the preparation of a food-grade product. According to the patent, the esterification is carried out between a free sterol and a fatty acid anhydride, with perchloric acid acting as a catalyst. The catalyst and reagent used cannot be accepted in a food process. In addition, the said patent relates to the fatty acid esters of only native plant sterols.

Many reagents which cannot be accepted as a food or for the production of a product intended as an additive for foods have been used in the preparation of sterol fatty acid esters. The use of, for example, chlorine (39), bromine (40), thionyl chloride (41) or anhydride derivatives of fatty acids is common. Of the methods previously patented, only the method of Baltes (Deutsches Patentamt, Offenlegungsschrift 2248921/Apr. 11, 1974) for the esterification of sterols present in oils and fats by a chemical interesterification technique fulfills the criteria of food processes. In the said patent, free sterol and an excess of fatty acid esters are added to a mixture of oil or fat, whereafter the entire fatty mixture is interesterified by a commonly known interesterification technique.

The present invention relates to the use of a sterol of an entirely different type for lowering the cholesterol level in serum. What is involved is fatty acid esters of 5α-saturated sterols, especially sitostanol fatty acid esters (sitostanol =24-ethyl-5α-cholestane- 3β-ol), which have been observed to lower cholesterol levels in serum with particular efficacy. The said esters can be prepared or used as such, or they can be added to foods, especially to the fatty part of a food. The sitostanol fatty acid ester mixture is prepared by hardening a commercial β-sitosterol mixture (sitosterol =24-ethyl-5-cholestene-3β-ol). β-sitostanol can be prepared by a prior-known cholesterol hardening technique by hardening β-sitosterol by means of a Pd/C catalyst in an organic solvent (43). This mixture has the approval of the FDA (Cytellin, Eli Lilly). A hardening degree of over 99% is achieved in the reaction. The catalyst used in the hardening is removed by means of a membrane filter, and the obtained sitostanol is crystallized, washed and dried. In accordance with the invention, the β-sitostanol mixture, which contains campestanol approx. 6%, is esterified with different fatty acid ester mixtures by a commonly known chemical interesterification technique (44, 45, 46). A methyl ester mixture of the fatty acids of any vegetable oil can be used in the reaction. One example is a mixture of rapeseed oil and methyl ester, but any fatty acids which contain approx. 2–22 carbon atoms are usable. The method according to the invention for the preparation of stanol fatty acid esters deviates advantageously from the previously patented methods in that no substances other than free stanol, a fatty acid ester or a fatty acid ester mixture, and a catalyst are used in the esterification reaction. The catalyst used may be any known interesterification catalyst, such as Na-ethylate.

It is also to be noted that in the method used in our application, contrary to the method of Baltes, referred to above, the fat itself is not interesterified. In this case the fatty part of a fat preparation or some other food will retain its natural properties. It should be noted further that the interesterified mixture can be added directly to fat-containing foods or be used as such. Since the stanol part of the mixture is non-absorbable, the energy content of the stanol fatty acid ester mixture is only 20–40% of the energy content of a conventional oil or fat, depending on the fatty acid composition. Thus the mixtures can be used advantageously also as substances decreasing the energy content of a food.

The action of β-sitostanol fatty acid esters on cholesterol absorption and on serum cholesterol levels has not been studied previously. The study on which this application is based investigated how plant sterol concentrations in serum were affected by sitostanol (composition: β-sitostanol 94% and campestanol 6%), a hardened form of sitosterol, dissolved in rapeseed oil, both a) free and b) in the form of a fatty acid ester. The test arrangement of the study is shown in Diagram 1 in Appendix 1. The first step for all groups was a rapeseed oil intervention (50 g/d), for the control group a rapeseed oil intervention for the duration of the test, and for the other groups a compound according to the test arrangement scheme, added to rapeseed oil.

Table 1 in Appendix 2 shows that an increase in the β-sitostanol concentration of food lowered the concentrations of both β-sitosterol and campesterol in serum, but did not produce a clear change in the serum β-sitostanol concentrations. The results also show that an intake of β-sitostanol in a soluble form—i.e. in the form of fatty acid esters—reduced the absorption of plant sterols more effectively than did free β-sitostanol taken in the same dosage. With respect to fatty acid esters of β-sitostanols there is additionally observed a clear dose response. It is evident that β-sitostanol also inhibits the absorption of β-sitosterol and campesterol, which can be seen as a decrease in their concentrations.

Respectively, the changes caused by stanol additions in the total and LDL serum cholesterol concentrations and in cholesterol absorption were also measured. The control group consumed ordinary rapeseed oil without stanol additions. Table 2 in Appendix 3 shows that cholesterol absorption was effectively reduced by a β-sitostanol fatty acid ester mixture (27.4%) even if the stanol intake was relatively low, 895 mg/day. The cholesterol absorption of the control group did not change. The action of free β-sitostanol and a β-sitostanol fatty acid ester mixture on the cholesterol concentration in serum, as compared with the control group, is seen in Table 3 in Appendix 4. A β-sitostanol fatty acid ester mixture decreased both total cholesterols and LDL cholesterol more effectively than did free and β-sitostanol. A β-sitostanol fatty acid ester mixture dissolved in rapeseed oil (3.2 g of β-sitostanol/day) decreased total cholesterol by 9.5% more and LDL cholesterol by 11.6% more than did rapeseed oil alone. Respectively, the HDL/LDL cholesterol ratio rose significantly, from 0.32 to 0.52.

The studies carried out show clearly that by the addition of β-sitostanol fatty acid esters to, for example, food fats, significant advantages can be achieved both in the national nutrition and in the treatment of hypercholesterollemia, since 1) the mixture lowers cholesterol values in serum, 2) the mixture does not increase serum plant sterol concentrations, 3) the mixture can be used daily as a fat substitute in cooking normal food, even in large doses (0.2–20 g/d), whereby the intake of energy from fat decreases.

Lipid changes caused by β-stanol fatty acid esters, observed in the study, are to be considered highly significant from the viewpoint of health. The significance of the results is emphasized by the possibility of using the compound alongside food preparations as part of ordinary cooking and an ordinary diet. Research results show that during an intervention diet the stanol level in serum does not rise, and that the levels of other plant sterols in the serum decrease. Thus the said β-stanol ester mixture is safe also for those few individuals who readily absorb all sterols or who have disturbances in sterol excretion. Furthermore, daily fat substitution decreases an individual's energy supply, since the effective stanol compound is not absorbed, i.e. it acts as a non-energy producing part of fat. There is no evidence of the said β-stanol ester mixture hampering the absorption of lipid-soluble vitamins or the vitamin levels in serum.

The uses of a sitostanol fatty acid ester mixture as a part of various fats and oils in fat-containing products are wide, since the physical properties of the mixture can be modified easily by altering the fatty acid composition of the mixture. In addition to this, the fatty acid composition of the β-stanol fatty acid ester mixture can be selected so as to contain large amounts of monoenes and polyenes, whereby its efficacy in lowering the cholesterol levels in serum are enhanced.

Since the β-sitostanol fatty acid ester mixture is prepared using raw materials belonging to normal food and production processes generally used in the food industry, there are no obstacles to the production and use of the compound.

EXAMPLE 1

A β-sitostanol ester mixture was prepared on a pilot scale. 6 kg of β-sitostanol which had been dried overnight at 60° C. was esterified with 8.6 kg of a rapeseed oil methyl ester mixture. The esterification was carried out as follows:

A mixture of β-sitostanol and rapeseed oil fatty acid methyl ester was heated in a reaction vessel at 90°–120° C. and under a vacuum of 5–15 mmHg. The drying was continued for an hour, 12 g of Na ethylate was added, and the reaction was continued for approx. 2 hours. The catalyst was destroyed by adding water to the mixture. After phase separation, the oil phase was dried under a vacuum.

A conversion of 98% was achieved in the reaction. The obtained ester mixture can be used as such as an additive in fats.

Instead of a mixture of rapeseed oil fatty acid esters it is possible to use in the reaction a methyl ester or a methyl ester mixture of the fatty acids of any vegetable oil, especially of fatty acids which contain approximately 2–22 carbon atoms.

EXAMPLE 2

Before the steam blowing of rapeseed oil, β-sitostanol ester mixture prepared in Example 1 was added, at 3, 6, and 13 % by weight, to the rapeseed oil. Mayonnaises containing the said fat mixtures at 65% were prepared.

| Mayonnaise: | % |
|---|---|
| fat mixture | 65.0 |
| thickening agent | 2.0 |
| salt | 1.0 |
| sugar | 3.0 |
| vinegar (10 wt. %) | 3.0 |
| mustard | 2.0 |
| water | 24.0 |
| total | 100.0 |

The mayonnaise was prepared by homogenization by a known manner using a Koruma homogenizer.

There were no problems in the preparation of the mayonnaises, and their properties tested by sense perception did not differ from those of conventional mayonnaises.

EXAMPLE 3

Before the steam blowing of oil, β-sitostanol ester mixture prepared in Example 1 was added, at 3 and 6% by weight, to the rapeseed oil.

The rapeseed oil to which the ester mixtures had been added remained clear at room temperature, and no permanent turbidity was observed in it when it was stored at refrigerator temperatures.

EXAMPLE 4

Other oils, such as sunflower, soybean, olive and corn oil, can also be used as the oil in the products according to Examples 2 and 3.

EXAMPLES 5

β-sitostanol ester mixture prepared in Example 1 was added, at 10 and 20% by weight, to the fatty part of a conventional soft margarine (composition: partly hardened soybean oil 35%, coconut oil 5%, rapeseed oil 60%) before the steam blowing of the fat mixture.

The DP (dropping point) and NMR values of the mixtures were analyzed

| 1) | the mixture as such |
| 2) | the mixture + ester mixture at 10% |
| 3) | the mixture + ester mixture at 20% |

| Mixture | | NMR values (%) | | | | | |
|---|---|---|---|---|---|---|---|
| | DP (°C.) | 10° C. | 20° C. | 30° C. | 35° C. | 40° C. | 45° C. |
| 1) | 31.9 | 24.2 | 11.6 | 2.7 | 0.7 | 0.0 | 0.0 |
| 2) | 30.4 | 21.4 | 10.0 | 1.8 | 0.2 | 0.0 | 0.0 |
| 3) | 29.6 | 25.4 | 9.2 | 2.0 | 0.6 | 0.0 | 0.0 |

A margarine which contained fat 80% was prepared by a generally known method. The physical and sense perceivable properties of the margarine corresponded to those of conventional margarines.

DIAGRAM 1
Test arrangement of the intervention study.
TEST GROUPS

```
(n = 22)

*-------------*--------------*----------*control (n = 8)
                  ---------------*  β-sitostanol
                                     (n = 7)
                  ---------------*----------*β-sitostanol ester
                                              (n = 7)
*-------------*--------------*----------*
0 wk.     6 wks.      15 wks.      21 wks.
INITIAL  EXPERI-     CONTINUATION PERIOD
         MENTAL
```

TABLE 1

Changes (%) caused during the experimental period in plant sterol levels in serum by β-sitostanol added to rapeseed oil, and during the continuation period with respect to β-sitostanol ester (3150 mg/d).

| Stanol added to rapeseed oil (mg/d) | Change (%) caused by the addition[1] | | |
|---|---|---|---|
| | Campesterol | β-sitosterol | β-sitostanol |
| β-sitostanol (895) | −18.4[x] | −13.0[x] | −0.6 |
| β-sitostanol ester (895)[2] | −28.4[x] | −23.4[x] | −10.3 |
| β-sitostanol ester (3150)[2] | −51.7[x] | −43.3[x] | −10.3 |

[1]Change in the table has been corrected by the %-change in the control group which had received rapeseed oil
[2]amount in free stanol
[x]change is significant as compared with the change in the control group, $p < 0.05$

TABLE 2

Effect of rapeseed oil and β-sitostanol ester dissolved in it on the absorption of cholesterol.

| Group (mg/d) | Cholesterol absorption at the intervention period | | Change (%) |
|---|---|---|---|
| | beginning | end | |
| Control | Rapeseed oil 29.4 | Rapeseed oil 30.4 | +3.4 |
| β-sitostanol ester | Rapeseed oil 29.2 | Rapeseed oil + β-sitostanol ester 21.2[xt] | −27.4 |

[x]change is significant, $p < 0.05$
[t]change is significant as compared with the change in the control group, $p < 0.05$
[1]amount in free stanol

TABLE 3

Effect in serum of β-sitostanol added to rapeseed oil on cholesterol levels

| Stanol added to rapeseed oil (mg/d) | Change (%) caused by the addition[1] | |
|---|---|---|
| | total cholesterol | LDL cholesterol |
| β-sitostanol (895) | −2.1 | −6.4 |
| β-sitostanol ester (3150) | −9.5[xt] | −11.6[t] |

[1]change has been corrected by the %-change in the control group which had received rapeseed oil

[x]change is significant, $p < 0.05$
[t]change is significant as compared with the change in the control group, $p < 0.05$ 1) Pollak, O. J., Reduction of blood cholesterol in man. Circulation, 7, 702–706, (1953).

2) Peterson, D. W., Effect of soybean sterols in the diet on plasma and liver cholesterol in chicks, Pric. Soc. Exp. Biol. Med., 78, 143–147, (1951).

3) Pollak, O. J., Succesful prevention of experimental hypercholesterolemia and cholesterol atheroscleroses in the rabbit, Circulation, 7, 696–701, (1953).

4) Farquhar, J. W. and Sokolow, M., Response of serum lipids and lipoproteins of man to beta-sitosterol and safflower oil—A long term study, Circulation, 17, 890, (1956).

5) Grundy, S. M., Ahrens, E. H. Jr., and Davignon, J., The interaction of cholesterol absorption and cholesterol synthesis in man, J. Lipid Res., 10, 304, (1969).

6) Oster, P., Schlierf, G., Heuck, C. C., Greten, H., Gundert-Remy, U., Haase, W., Klose, G., Nothelfer, A., Raetzer, H., Schellenberg, B. und Schmidt-Gayk, H., Sitosterin bei familiären Hyperlipoproteinämie Typ II. Eine randomisierte gekreuzte Doppelblindstudie, Dtsch. Med. Wschr., 101, 1308–1311, (1976).

7) Grundy, S. M., Dietary and drug regulation of cholesterol metabolism in man, pp. 127–159 in "Lipid Pharmacology, Vol II", Eds: Paoletti, R and Glueck, C. J., Academic Press, New York, 1976.

8) Lees, A. M., Mok, H. Y. I., McCluskey, M. A., Grundy, S. M., Plant sterols as cholesterol lowering agents: clinical trials in patients with hypercholesterolemia and studies of sterol balance, Atherosclerosis, 28, 325–338. (1977).

9) Schwartzkopf, W. and Jantke, H.-J., Dosiswirksamkeit von Beta-sitosterin bei Hypercholesterinemien der Typen II A und II B, Munch. Med. Wschr., 120, 1575, (1969).

10) Tilvis, R. S., Miettinen, T. A., Serum plant sterols and their relation to cholesterol absorption, Am. J. Clin. Nutr., 43, 92–97, (1986).

11) Miettinen, T. A., Tilvis, R. S., Kesäniemi, Y. A., Serum plant sterols and cholesterol precursors reflect cholesterol absorption and synthesis in volunteers of a randomly selected male population, Am. J. Epidem., 131, (1), 20–31. (1990).

12) Färkkilä, M. A. , Tilvis, R. S. , Miettinen, T. A., Regulation of plasma plant sterols levels in patients with gut resections, Scand. J. Clin. Lab. Invest., 48, 715–722, (1988).

13) Grundy, S. M., Mok, H. Y. I., Effects of low dose phytosterols on cholesterol absorption in man, pp. 112–118 in "Lipoprotein metabolism". Ed. Greten, H., Berlin, Heidelberg, New York: Springer-Verlag, 1976

14) Kudchodkar, B. J., Horlick, L., Sodhi, H. S., Effects of plant sterols on cholesterol metabolism in man, Atherosclerosis, 23, 239, (1976).

15) Ikeda, I., Tanaka, K., Sugano, M., Vahouny, G. V., Gallo, I. L., Inhibition of cholesterol absorption in rats by plant sterols, J. Lipid Res., 29, 1573–1582, (1988).

16) Ikeda, I., Tanaka, K., Sugano, M., Vahouny, G. V., Gallo, I. L., Discrimination between cholesterol and sitosterol for absorption in rats, J. Lipid Res., 29, 1583–1592, (1988).

17) Ikeda, I., Tanabe, Y. and Sugano, M., Effects of sitosterol and sitostanol on micellar solubility of cholesterol, J. Nutr. Sci. Vitaminol., 35, 361–369, (1989).

18) Ikeda, I., Sugano, M., Comparison of absorption and metabolism of beta-sitosterol and beta-sitostanol in rats, Atherosclerosis, 30, 227, (1978).

19) Sugano, M., Marioka, H. and Ikeda, I., A comparison of hypocholesterolemic activity of β-sitosterol and β-sitostanol in rats, J, Nutr., 107, 2011–2019, (1977).

20) Heinemann, T., Leiss, O., von Bergman, K., Effects of low-dose sitostanol on serum cholesterol in patients with hypercholesterolemia, Atherosclerosis, 61, 219–223, (1986).

21) Lees, R. S., Lees, A. M., Effects of sitosterol therapy on plasma lipids and lipoprotein concentrations, pp. 119–124 in "Lipoprotein metabolism". Ed: Greten, H., Berlin, Heidelberg, New York: Springer-Verlag, 1976.

22) Mattson, F. H., Volpenhein, R. A. and Erickson, B. A.: Effect of plant sterol esters on the absorption of dietary cholesterol, J. Nutr., 107, 1139–1146, (1977).

23) Heinemann, T., Pietruck, B., Kullak-Ublick, G., von Bergman, K., Comparison of sitosterol and sitostanol on inhibition of intestinal cholesterol absorpiton, Agents Actions (Suppl), 26, 117–122, (1988).

24) Heinemann, T., Kullak-Ublick, G.-K., Pietruck, B., von Bergmann, K., Mechanisms of action of plant sterols on inhibition of cholesterol absorption, Eur. J. Clin. Pharmacol., 40 Suppl. 1, S50–S63, (1991).

25) Mattson, F. H., Grundy, S. M., Crouse, J. R., Optimizing the effect of plant sterols on cholesterol absorption in man, Am. J. Clin. Nutr., 35, 697–700, (1982).

26) Kesäniemi, Y. A., Ehnholm, C., Miettinen, T. A., Intestinal cholesterol absorption efficiency in man is related to apoprotein E phenotype, J. Clin. Invest., 80, 578–581, (1987).

27) Kesäniemi, Y. A., Miettinen, T. A., Metabolic epidemiology of plasma cholesterol, Ann. Clin. Res., 20, 26–31, (1988).

28) Ehnholm, C., et al., Apolipoprotein polymorphism in the Finnish population: gene frequencies and relation to lipoprotein concentrations, J. Lipid. Res. 27, 227–235, (1986).

29) Miettinen, T. A., Gylling, H., Vanhanen, H., Serum cholesterol response to dietary cholesterol and apoprotein E phenotype, Lancet, 2, 1261, ( 1988 ).

30) Gould, G., Absorbability of beta-sitosterol, Trans. N.Y. Acad. Sci., 2, 129, (1955).

31) Gould, R. G., Jones, R. J., LeRoy, G. W., Wissler, R. W., Taylor, C. B., Absorbability of β-sitosterol in humans, Metabolism, 18, 652–662, (1969).

32) Salen, G., Ahrens, E. J., Grundy, S. M., Metabolism of β-sitosterol in man, J. Clin. Invest., 49, 952–67, (1970).

33) Salen, G., Kwiterowich, P. O. Jr, Shefer, S., Tint, G. S., Horak, I., Shore, V., Dayal, B., Horak, E. Increased plasma cholestanol and 5α-saturated plant sterol derivatives in subjects with sitosterolemia and xanthomatosis, J. Lipid Res., 26, 203–209, (1985).

34) Salen, G., Shore, V., Tint, G. S., Forte, T., Shefer, S., Horak, I., Horak, E., Dayal, B., Nguyen, L., Batta, A. K., Lindgren, F. T. and Kwiterowich, P. O., Jr., Increased sitosterol absorption, decreased removal and expanded body pools compensate for reduced cholesterol synthesis in sitosterolemia with xanthomatosis. J. Lipid Res., 30, 1319–1330, (1989).

35) Miettinen, T. A. Phytosterolemia, xanthomatosis and premature atherosclerosis desease: a case with high plant sterol absorption, impaired sterol elimination and low cholesterol synthesis, Eur. J. Clin. Invest., 10, 27–35, (1980).

36) Nikkilä, K., Miettinen, T. A., Serum cholesterol precursors, cholestanol and plant sterols in PBC, Scand. J. Gastroenterl., 23, 967–972, (1988).

37) Miettinen, T. A., Siurala, M., Bile salts, sterols, asterol esters, glycerides and fatty acids in micellar and oil phases of intestinal contents during fat digestion in man, Z. Klin. Chem. Biochem., 9, 47–52, (1971).

38) Hassan, A. S., Rampone, A. J., Intestinal absorption and lymphatic transport of cholesterol and β-sitostanol in the rat, J. Lipid Res., 20, 646–653, (1979).

39) Kuksis, A., Beveridge, J. M. R., J. Org. Chem, 25:1209, (1960).

40) Saroja, M., Kaimal, T. N. B., A convienent method of esterification of fatty acids. Preparation of alkyl esters, sterol esters, wax esters and trialcylglycerols, Synthetic communications, 16, 1423–1430, (1986).

41) Prabhudesai, A. V., A simple method for the preparation of cholesteryl esters, Lipids, 12, 242–244, (1977).

42) Lentz, B. R., Barenholz, Y., Thompson, T. E., A simple method for the syntesis of cholesterol esters in high yield, Chemistry and Physics of Lipids, 15, 216–221, (1975).

43) Augustine, R. L. and Reardon Jr., E. J., The palladium catalyzed hydrogenation of cholesterol, Organic preparations and procedures 1(2), 107–109, (1969).

44) Sreenivasan, B., Interesterification of fats, J. Am. Oil Chemists' Soc., 55, 796–805 (1978).

45) Lo, Y. C. and Handel, A. P., Physical and chemical properties of randomly interesterified blends of soybean oil and tallow for use as margarine oils, J. Am. Oil Chemists' Soc., 60, 815–818, (1983)

46) Chobanov, D., Chobanova, R., Alterations in glyceride composition during interesterification of mixtures of sunflower oil with lard and tallow, J. Am. Oil Chemists' Soc., 54, 47–50 (1977).

We claim:

1. The method of reducing the absorption of cholesterol into the bloodstream comprising orally introducing into the body an effective amount of a substance containing a β-sitostanol fatty acid ester prepared by the interesterification of β-sitostanol with a fatty acid ester containing between 2 and 22 carbon atoms in the presence of an interesterification catalyst.

2. The method according to claim 1, wherein the interesterification of β sitostanol is carried out in a solvent free food grade process.

3. The method according to claim 2, wherein the interesterification occurs at a temperature of approximately 90°–120° C. and a vacuum of approximately 5–15 mmHg.

4. The method according to claim 3, wherein the catalyst is sodium ethylate.

5. The method of claim 1, wherein the fatty acid ester comprises a mixture of fatty acid esters.

6. The method according to claim 1, wherein the β sitostanol is prepared by hydrogenation of a commercial β sitosterol mixture.

7. The method according to claim 1, wherein the interesterification is carried out in the presence of a stoichiometric excess of the fatty acid ester.

8. The method according to claim 1 wherein an effective amount of the substance is between about 0.2 and about 20 grams per day.

* * * * *